US005593768A

United States Patent [19]
Gessner

[11] Patent Number: 5,593,768
[45] Date of Patent: Jan. 14, 1997

[54] NONWOVEN FABRICS AND FABRIC LAMINATES FROM MULTICONSTITUENT FIBERS

[75] Inventor: Scott L. Gessner, Encinitas, Calif.

[73] Assignee: Fiberweb North America, Inc., Simpsonville, S.C.

[21] Appl. No.: 233,634

[22] Filed: Apr. 26, 1994

Related U.S. Application Data

[63] Continuation of Ser. No. 783,696, Oct. 30, 1991, abandoned, which is a continuation-in-part of Ser. No. 344,744, Apr. 28, 1989, Pat. No. 5,108,827.

[51] Int. Cl.$^6$ .............................. D04H 3/14; D04H 3/16
[52] U.S. Cl. ........................ 428/286; 428/287; 428/288; 428/296; 428/302
[58] Field of Search ............................ 428/286, 287, 428/288, 296, 302

[56] References Cited

U.S. PATENT DOCUMENTS

| | | |
|---|---|---|
| 3,112,160 | 11/1963 | Rush . |
| 3,369,057 | 2/1968 | Twilley . |
| 3,382,305 | 5/1968 | Breen . |
| 3,595,731 | 8/1968 | Kauffman . |
| 3,602,892 | 8/1971 | Norris et al. . |
| 3,620,892 | 11/1971 | Wincklhofer . |
| 3,672,802 | 6/1972 | Matsui et al. . |
| 3,968,307 | 7/1976 | Matsui et al. . |
| 4,211,816 | 7/1980 | Booker et al. . |
| 4,280,860 | 7/1981 | Shen et al. . |
| 4,296,022 | 10/1981 | Hudson . |
| 4,361,609 | 11/1982 | Gerlach et al. . |
| 4,381,335 | 4/1983 | Okamoto . |
| 4,436,780 | 3/1984 | Hotchkiss et al. . |
| 4,477,516 | 10/1984 | Sugihara et al. . |
| 4,500,384 | 2/1985 | Tomioka et al. . |
| 4,563,504 | 1/1986 | Hert et al. . |
| 4,568,506 | 2/1986 | Kiriyama et al. . |
| 4,584,347 | 4/1986 | Harpell et al. . |
| 4,632,861 | 12/1986 | Vassilatos . |
| 4,634,739 | 1/1987 | Vassilatos . |
| 4,657,804 | 4/1987 | Mays et al. . |
| 4,749,423 | 6/1988 | Vaalburg et al. . |
| 4,766,029 | 8/1988 | Brock et al. . |
| 4,769,279 | 9/1988 | Graham . |
| 4,770,925 | 9/1988 | Uchikawa et al. . |
| 4,797,318 | 1/1989 | Brooker et al. . |
| 4,806,598 | 2/1989 | Morman . |
| 4,822,678 | 4/1989 | Brody et al. . |
| 4,830,904 | 5/1989 | Gessner et al. . |
| 4,839,228 | 6/1989 | Jezic et al. . |
| 4,851,284 | 7/1989 | Yamanoi et al. . |
| 4,861,652 | 8/1989 | Lippert et al. . |
| 4,874,666 | 10/1989 | Kubo et al. . |
| 4,883,707 | 11/1989 | Newkirk . |
| 4,902,553 | 2/1990 | Hwang et al. . |
| 4,908,052 | 3/1990 | Largman et al. . |
| 4,916,005 | 4/1990 | Lippert et al. . |
| 5,059,482 | 10/1991 | Kawamoto et al. . |
| 5,073,436 | 12/1991 | Antonacci et al. . |
| 5,108,827 | 4/1992 | Gessner . |
| 5,130,196 | 7/1992 | Nishio et al. . |
| 5,133,917 | 7/1992 | Jezic et al. . |
| 5,294,482 | 3/1994 | Gessner ............................ 428/287 |

FOREIGN PATENT DOCUMENTS

| | | |
|---|---|---|
| 661784 | 9/1965 | Belgium . |
| 1199746 | 1/1986 | Canada . |
| 277707 | 10/1988 | European Pat. Off. . |
| 340982 | 11/1989 | European Pat. Off. . |
| 394954 | 10/1990 | European Pat. Off. . |
| 405793 | 1/1991 | European Pat. Off. . |
| 416620 | 3/1991 | European Pat. Off. . |
| 63-165511A | 8/1988 | Japan . |

OTHER PUBLICATIONS

P. M. Subramanian, et al., "Laminar Morphology in Polymer Blends Structure and Properties", *Antec*, 1986, pp. 301–303.
D. R. Paul, Fibers from Polymer Blends, pp. 168–215.
W. H. Skoroszewski, "Parameters Affecting Processing of Polymers and Polymer Blends", *Plastics & Polymers*, vol. 40, No. 147; Jun. 1972, pp. 142–152.
S. B. Warner, "Thermal Bonding of Polypropylene Fibers", *Textile Research Journal*, Mar. 1989, pp. 151–159.

*Primary Examiner*—James C. Cannon
*Attorney, Agent, or Firm*— Bell, Seltzer, Park & Gibson

[57] ABSTRACT

The present invention provides a nonwoven fabric laminate comprising a thermally-bonded multiconstituent fiber nonwoven web. The multiconstituent fiber is composed of a highly dispersed blend of at least two different thermoplastic polymers which are present as a dominant continuous phase and at least one noncontinuous phase dispersed therein. The noncontinuous phase exists as an elongated fibrillar polymer domain oriented generally in the direction of the fiber axis. The polymer of the noncontinuous phase has a melting temperature below that of said continuous phase, and the lower melting noncontinuous phase comprises from about 2.5 to about 20 percent by weight of the fiber. The fabric laminate also comprises at least one other web bonded to the multiconstituent fibers of the thermally bonded nonwoven web and a multiplicity of thermal bonds formed from the polymer of said multiconstituent fibers and bonding the multiconstituent fibers of said thermally bonded web to said at least one other web.

29 Claims, 4 Drawing Sheets

NONWOVEN FABRICS AND FABRIC LAMINATES FROM MULTICONSTITUENT FIBERS

CROSS-REFERENCE TO RELATED APPLICATIONS

This application is a continuation of commonly-owned application Ser. No. 07/783,696 filed Oct. 30, 1991, now abandoned, which in turn, is a continuation-in-part of commonly-owned application Ser. No. 07/344,744 filed Apr. 28, 1989, now U.S. Pat. No. 5,108,827. The benefit of the earlier filing dates of these applications is claimed under 35 U.S.C. 120.

BACKGROUND OF THE INVENTION

This invention relates to nonwoven fabrics and fabric laminates made by thermally bonding fibrous webs formed from certain types of multiconstituent fibers. Thermal bonding of the nonwoven fabrics may be accomplished by calender or "through air" techniques or ultrasonically. The multiconstituent fibrous webs may contain other fibers in addition to the thermoplastic multiconstituent fibers. The nonwoven fabrics and fabric laminates produced according to the present invention may be optimized as to softness and strength characteristics.

Nonwoven fabrics and fabric laminates are widely used in a wide variety of everyday applications, as for example, as components in absorbent products such as disposable diapers, adult incontinence pads and sanitary napkins; in medical applications such as surgical gowns, surgical drapes, sterilization wraps; and in numerous other applications such as disposable wipes, industrial garments, housewrap, carpets and filtration media.

By combining two or more nonwoven fabrics of different types, nonwoven fabric laminates have been developed for a variety of specific end use applications. For example, nonwoven fabric laminates have been developed to serve as a barrier to penetration by liquids or microorganisms. Barrier fabric laminates of this type typically comprise one or more microfibrous (for example meltblown) polymer layers, combined with one or more layers of another type of nonwoven fabric, such as a spunbonded nonwoven fabric. Nonwoven barrier fabrics of this general type are used as medical and industrial garments, CSR wrap, surgical drape and housewrap. Specific examples of such fabrics are described in U.S. Pat. Nos. 3,676,242, 3,795,771, 4,041,203, 4,766,029 and 4,863,785.

While nonwoven fabrics of this general type have found widespread use in various applications, as noted above, there are many applications in which it would be desirable to have a fabric with improved softness, drape and/or strength characteristics.

The present invention uses certain multiconstituent fibers in the production of nonwoven fabrics and fabric laminates, and has thereby achieved improvements in softness, drape, strength and other characteristics. The multiconstituent fibers are of the random matrix type and are formed by melt extruding a highly dispersed blend of two or more polymers having low affinity for one another.

Various types of random matrix multiconstituent fibers are described in the literature. For example, in some instances blends of different polymers are extruded from the orifices of spinnerets in order to make fibers containing "free form" microfibrils which can then be separated from the matrix polymer. Note for example, Breen U.S. Pat. No. 3,382,305, Twilley U.S. Pat. No. 3,369,057, and Allan (U.S. patent application Ser. No. 07/220,203).

A few references cite fibers and nonwoven fabrics made from polymer blends wherein the dominant continuous phase is lower melting than the dispersed noncontinuous phase; see Kubo (European Patent Application No. 0277707), Wincklhofer U.S. Pat. No. 3,620,892 and Vassilatos U.S. Pat. No. 4,632,861. By definition, to thermally bond such fibers, portions of the continuous fiber phase are raised to temperatures where partial molecular relaxation of the continuous lower melting phase occurs. Relaxation occurs not only at the bond site proper but also in the fiber region surrounding the bond site which is responsible for distributing a load or strain throughout the bonded fiber network. Although thermally-bonded nonwoven fabrics can be made from these materials, strength is compromised.

Published European Application 405,793 describes fibers, films and articles made from a blend of compatible polymers, including a non-crystalline mesomorphous polypropylene and another polymer compatible therewith. Other melt spun fibers formed from polymer blends are described in Brody et al. U.S. Pat. No. 4,822,678, Jezic et al. U.S. Pat. No. 4,839,228 and in Published European Patent Application 416,620.

Finally, Graham U.S. Pat. No. 4,769,279 refers to meltblown fibers and fabrics made from blends of ethylene/ acrylic copolymer with a second fiber-forming polymer such as a polyvinyl, a polyamide, and a polyolefin. Graham does not disclose thermally-bonded nonwoven fabrics from engineered fibers, however. Furthermore, the Graham disclosure is limited to blends based upon low viscosity ethylene/acrylic copolymers.

SUMMARY OF THE INVENTION

The present invention provides nonwoven fabrics and fabric laminates made of engineered multiconstituent fibers. By "engineered" fibers, we mean oriented fibers made by melt-spinning a highly dispersed blend of at least two different thermoplastic polymers which are present as a dominant continuous phase and at least one noncontinuous phase dispersed therein. The noncontinuous phase exists as an elongated fibrillar polymer domain oriented generally in the direction of the fiber axis. The polymer of the noncontinuous phase or phases has a melting temperature below that of the continuous phase. Preferably, the lower melting noncontinuous phase or phases comprises from about 2.5 to about 20 percent by weight of the fiber. The fabric laminate also comprises at least one other web which is bonded to the multiconstituent fibers of the thermally bonded nonwoven web by a multiplicity of thermal bonds. These thermal bonds are formed from the polymer of the multiconstituent fibers. In addition to bonding the two webs together, these thermal bonds also bond together the multiconstituent fibers of the thermally bonded web to give it strength and structural integrity. The thermal bonds of the multiconstituent fiber webs in accordance with the present invention have been shown to provide superior strength than is obtained in thermally bonded webs formed from conventional single constituent fibers. The present invention provides for development of good bond strength through a bond that is both adhesive as well as cohesive, as opposed to a principally cohesive bond.

In one particular embodiment, the present invention provides a nonwoven fabric laminate comprised of first and second spunbonded webs of multiconstituent fiber, and at least one meltblown microfibrous web disposed between these spunbonded webs and bonded thereto. The multiconstituent fiber of the spunbonded webs comprises continuous filaments formed of a highly dispersed blend of at least two different thermoplastic polymers which are present as a dominant continuous phase and at least one noncontinuous phase dispersed therein, with the polymer of the noncontinuous phase having a melting temperature below that of the continuous phase. The fabric includes a multiplicity of thermal bonds formed in the spunbonded webs from the polymer of the multiconstituent fiber thereof, with the thermal bonds bonding the continuous filaments of the spunbonded webs to one another and also bonding the spunbonded webs to said at least one meltblown microfibrous web.

Laminates in accordance with the present invention may be made by combining nonwoven fabrics made from the multiconstituent fiber as described herein with films, paper, tissue, woven fabrics, or nonwoven fabrics, including meltblown nonwovens. Such laminates are suitable for use in filtration media, medical and clean room garments, CSR wrap, absorbent article backsheets, and other barrier structures.

DESCRIPTION OF THE PREFERRED EMBODIMENTS

Figure 1:
FIG. 1 is a photomicrograph of a cross-section of a 20-micron-diameter fiber enlarged 25,000 times.

Biconstituent or multiconstituent fibers that may be used to make fabrics and laminates according to the present invention are those which are spun from an intimately mixed blend of different polymers which have a low affinity for each other. Thus, at least two of the polymers in the blend form distinct phases which can be visually identified under high magnification. Because they form distinct phases, they have been described in the parent application as being immiscible. However, in reality, the polymers which are useful to form multiconstituent fibers in accordance with the present invention are not necessarily completely immiscible in the molten state, but usually have limited solubility in one another and are therefore more accurately described as having a low affinity for one another.

The choice of polymers is limited to those that are thermoplastic (including many elastomers) and that have a melt temperature below 350° C., preferably below 275° C. Examples of polymers that can be used are:

Polyethylenes:
  Low density PE (0.90–0.940 g/cc) (long-chain branched PE)
  LLDPE (made with $C_3$–$C_{12}$ alpha-1-olefin or copolymers or 4-methyl-1-pentene)
  Medium and high density PE (0.940–0.960 g/cc)
  Homopolymer or with copolymers described above Atactic polypropylene
Polypropylene (at least 90% isotactic)
Co- and terpolymers of polypropylene (e.g. with ethylene, butene, pentene, 4-methyl-1pentene, etc.)
Block copolymers of ethylene and propylene
Random copolymers of ethylene and propylene
Polybutylene
Poly(4-methyl-1-pentene) [TPX]
Polycarbonate
Polyesters, e.g. poly(oxyethyleneoxyterephthaloyl)
Polyamides, e.g. poly(imino-1-oxohexamethylene) [Nylon 6] & Poly(iminohexamethyleneiminoadipoyl) [Nylon 66]
Poly(oxymethylene)
Polystyrene
Styrene copolymers, e.g., styrene acrylonitrile [SAN]
Polyphenylene ether
Polyphenylene oxide [PPO]
Polyetheretherketone [PEEK]
Polyetherimide
Polyphenylene sulfide [PPS]
Poly(vinyl acetate) [PVA]
Poly(methyl methacrylate) [PMMA]
Poly(methacrylate) [PMA]
Ethylene acrylic acid copolymer
Polysulfone The biconstituent or multiconstituent fibers that make up a significant portion of the webs to be thermally bonded according to the present invention must exhibit a high degree of dispersion. Factors which determine the level of dispersion and phase morphology of the dispersed phase or phases in blend fibers are discussed in detail by D. R. Paul in "Polymer Blends," Volume 2, Chapter 16 Briefly, the dispersed-phase morphology of the blend fiber is dependent upon the relative rheologies of the blend components, the interfacial tension between the two or more phases, the polymer volume ratio, and the three stages of the blend melt preparation and processing: melt dispersion, extrusion, and extrudate draw-down prior to solidification. In general, the largest domains in the blend will exist when the polymer ratio is near 1.0; at this point the polymers are nearly co-continuous. The domain size of the discontinuous phase will decrease as the ratio deviates from 1.0, given that the quantity of work "mixered" into the blend and the melt-spinning conditions remain constant.

Preferably, the noncontinuous phase or phases comprise from about 2.5 to 20 percent by weight of the fiber, and most desirably, from about 5 to 15 percent by weight. As such, the noncontinuous phase exists as an elongated fibrillar polymer domain oriented generally in the direction of the fiber axis. The mean of the polymer domain cross-sections of the noncontinuous phase or phases is less than 0.1% of the cross-sectional area of the fiber, and the fiber is configured such that the noncontinuous phase or phases occupy a substantial portion of the fiber surface. The polymer of the noncontinuous phase or phases has a Polymer Melt Temperature (PMT) at least 10° C. below the PMT of the continuous phase, and for many applications, especially where both constituents are polyolefins, it is preferable that the noncontinuous phase or phases have a polymer melting temperature in the range of 30° C. to 50° C. below the PMT of the continuous phase.

Thermal bonding work on fabrics made from biconstituent polyethylene/polypropylene staple fibers has demonstrated weak bonding at calender temperatures at and just above the melting point of the lower melting polyethylene constituent. One of the problems with biconstituents, in general, in thermal bonding can be that the lower melting component is distributed throughout the fiber matrix rather than being concentrated at the surface where it can be active in bonding. Therefore, fibers according to the present invention are often preferably fibers with increased surface-to-volume ratios, with the ultimate being a ribbon-shaped fiber. High surface/volume fibers make more of the lower melting component available for bonding, which ultimately results in higher tensile strength fabrics and laminates.

FIG. 1 is a TEM photomicrograph of a $RuO_4$-stained polyethylene/polypropylene fiber cross-section, enlarged 25,000 times. The dark domains are polyethylene (PE); the lighter domains are the continuous polypropylene (PP) phase. The photograph demonstrates how well the PE phase is dispersed in the PP phase. It is interesting to note how the PE phases become circumferentially elongated at the fiber surface.

Fibers used to make fabric in accordance with the present invention may be processed as follows: two or more polymers, selected to meet the melting point differential that characterizes the present invention, are combined and blended to form a dispersion. The dispersion is then either melt-spun into fibers, which may be formed into webs for instance by carding, airlaying, or wetlaying, or melt-spun directly into fibrous webs by a spunbonding process. The webs are then thermally-bonded to transform them into strong soft bi- or multiconstituent fiber nonwoven fabrics. The specific fabric characteristics will be dependent on the choice of precursor polymer or fiber and processing conditions. The nonwoven fabrics may then be laminated into structures having a variety of desirable end-use characteristics.

Appropriate combinations of polymers combined to make the fibers used in accordance with the present invention are intimately blended before being melt-spun into fibers or fibrous webs. A high degree of mixing is usually necessary in order to prepare blends that will satisfy the degree of dispersion criteria that characterizes the fibers used according to the present invention. For good spinnability at high linear fiber velocity (e.g., on the order of 3,000 meters/minute or greater) and/or at high levels of the dispersed polymer, (e.g., greater than 20–25 percent), it is desirable to use a polymer mixer apparatus. Among the commercially available mixers that can be used are the Barmag 3DD three-dimensional dynamic mixer supplied by Barmag AG of West Germany and the RAPRA CTM cavity-transfer mixer supplied by the Rubber and Plastics Research Association of Great Britain. At lower linear fiber velocities (e.g., 500 meters per minute or below) or with relatively low levels of dispersed polymer, the mixing requirements are less critical, and a sufficiently high degree of mixing can be achieved in the extruder without requiring a separate mixer apparatus.

The process for manufacturing the webs to be thermally or sonically bonded according to the present invention can be any of the known commercial processes for making nonwoven fabrics, including processes that use mechanical, electrical, pneumatic, or hydrodynamic means for assembling fibers into a web, for example carding, wetlaying, carding/hydroentangling, wetlaying/hydroentangling, and spunbonding.

Thermally-bonded nonwoven fabrics and laminates according to the present invention exhibit advantages over similar homofilament-based nonwovens. A few of those advantages are higher tensile strength/basis weight ratio, and higher tear resistance/basis weight ratio. The multiconstituent fibers of the invention can provide substantial advantages when used in one or more layers of laminate structures and particularly in laminate structures in which lamination of layers is achieved by thermal bonding. In barrier fabrics which employ one or more layers of microfine fibers, such as melt blown fibers, as a barrier layer, bonding of a multiconstituent fiber layer to the microfine fiber layer can be accomplished without substantial melting of the microfine fiber layer when a multiconstituent fiber is used having a dispersed constituent of lower melting point than the microfine fiber layer. In addition, the structural benefits achieved by the higher melting component of the multiconstituent fiber can often be substantially preserved despite the fusion of the multiconstituent fibers at areas of thermal bonding.

Advantageously, the multiconstituent fiber is provided as a continuous filament or a staple fiber non-woven web for bonding to a microfine fiber layer. Continuous filament nonwoven webs, i.e., spunbonded webs, can be provided with or without prebonding for lamination to a microfine fiber layer. Similarly, a multiconstituent staple fiber web can be provided with or without prebonding for thermal lamination to a microfine fiber layer.

Spunbonded/meltblown/spunbonded (SMS) laminate fabrics produced using multiconstituent fibers in the spunbonded component in accordance with the invention have a number of advantages over conventional SMS fabrics which employ homofilaments in the spunbonded layers. Such fabrics can be manufactured at a lowered bonding temperature, due to the lower softening temperature of the lower melting component of the polymer blend. This broadens the temperature range (i.e. "bonding temperature window") at which bonding of the SMS laminate can be effectively carried out, thereby reducing the criticality of bonding temperature as an operating parameter in manufacturing. Furthermore, the bond that is created occurs by melting and flowing of the spunbonded layer rather than the meltblown layer. This reduces the likelihood of disrupting the barrier properties of the meltblown layer. The resulting bond sites are physically and thermomechanically different from those resulting from bonding a homofilament-based spunbonded fabric to a meltblown layer, as is done in known commercial SMS fabrics. The improved bonding results in a fabric with improved resistance to delamination.

The multiconstituent fibers used in SMS laminate fabrics intended for medical applications in which the fabric is subjected to autoclaving for sterilization are preferably formed from a blend of isotactic polypropylene and a polyethylene, preferably linear low density polyethylene. The polyethylene content is preferably from 2.5 to 20 percent by weight of the fiber, and most desirably from 5 to 15 percent. At higher polyethylene contents, the fabric takes on an undesirable ironed appearance and exhibits an increase in stiffness when subjected to autoclaving temperatures (e.g., 110° C.). At 25 percent polyethylene and higher, the fabric may melt when subjected to autoclaving.

SMS laminate fabrics in accordance with the present invention have significantly better flexibility than commercially available competitive SMS laminate fabrics. For application as a sterilization wrap, fabric flexibility is an important performance feature. Without adequate flexibility, the fabric has a resistance to folding, called "snap-back," such that the fabric will try to unfold back into a flat sheet when wrapped around an object. When using large sheets for wrapping big instruments, this presents a significant problem to users.

Fabric stiffness may be quantitatively measured in terms of its flexural rigidity, using ASTM standard test method D1388 (Option A—Cantilever test). This test measures the free bending of a strip of fabric projecting from the edge of a horizontal surface. Measurements are made in the in the machine direction (MD) and in the cross machine direction (CD). The free bending length measurement is then entered into a calculation of Flexural Rigidity which corrects for differences in basis weight.

$$\text{Flexural Rigidity} = G = W \times (O/2)^3$$

where

W=basis weight

O=free bending length

SMS laminate fabrics in accordance with the present invention have been shown to have a flexural rigidity of 1000 or less in the machine direction and 300 or less in the cross machine direction.

The multiconstituent fibers used in nonwoven fabric laminates intended for medical applications in which the fabric is sterilized by gamma radiation may be formed from a blend of a polyamide (e.g. nylon 6 or nylon 66) and up to about 50 percent by weight of a polyethylene, preferably linear low density polyethylene. Such fabric laminates exhibit good gamma stability and have advantages over a homofilament nylon fiber construction in softness (hand) and bonding. For example, a surgical gown fabric may be formed from an SMS laminate construction in which the filaments of the spunbond fabric component are a blend of nylon 6 with linear low density polyethylene, and the microfibrous component is formed of polypropylene meltblown microfibers. Preferably the blend contains up to about 20 percent polyethylene. Such nonwoven fabric laminates may also be formed from multiconstituent fibers of a blend of polyester and polyethylene.

Thermally bonded nonwoven fabrics, laminates and composite structures having advantageous properties for various other specific applications can be formed containing multiconstituent fibers from blends of:

(a) At least two polymer components where the dominant continuous phase is an isotactic polypropylene with a melt flow rate (MFR) greater than 20 g/10 minutes and the noncontinuous dispersed phase is linear low density polyethylene (preferably with a melt index (MI) of greater than 100 g/10 minutes.

(b) At least two polymer components where the dominant continuous phase is a co- or ter- polymer of polypropylene and the noncontinuous dispersed phase is a polyethylene (low density polyethylene, linear low density polyethylene or high density polyethylene).

(c) At least two polymer components where the dominant continuous phase is an isotactic polypropylene and the noncontinuous dispersed phase is a high density polyethylene (>0.945 g/cc), where the ratio of HDPE to PP is less than 0.6:1.

(d) At least two polymer components where the dominant continuous phase is an isotactic polypropylene and the noncontinuous dispersed phase is a low density polyethylene (LDPE) where the LDPE is present in an amount greater than 5% and less than 35% by weight.

(e) At least two polymer components where the dominant continuous phase is an isotactic polypropylene and the noncontinuous dispersed phase is linear low density polyethylene (LLDPE) where the LLDPE is present in an amount less than 20% by weight.

(f) At least two polymer components where one phase is poly(4-methyl,1-pentene) (TPX) and another phase is an olefin polymer, copolymer or terpolymer and where the ratio is 1:99 to 99:1.

(g) At least two polymer components where the dominant continuous phase is a polyamide polymer and the noncontinuous dispersed phase is linear low density polyethylene (LLDPE) where the LLDPE is present in an amount less than 20% by weight.

EXAMPLE 1

Biconstituent staple fiber was prepared by dry blending 40% by weight of an ethylene/1-octene linear low density polyethylene [LLDPE] having a melt index of 26.5 and a density of 0.940 grams/cc with 60% by weight of controlled rheology polypropylene [PP] having a melt flow rate of 26. The dry blend [PP/LLDPE] was fed into a single-screw extrusion system equipped with a Barmag 3DD intensive mixer. Filaments were extruded and drawn to a final denier per filament of approximately 2.0. Line speeds and cold draw ratios were adjusted to produce two filament samples, one having 2 X cold draw and another having 3.5 X draw. Refer to Table I, samples 8319-2 and 8319-3, respectively.

Figure 2:
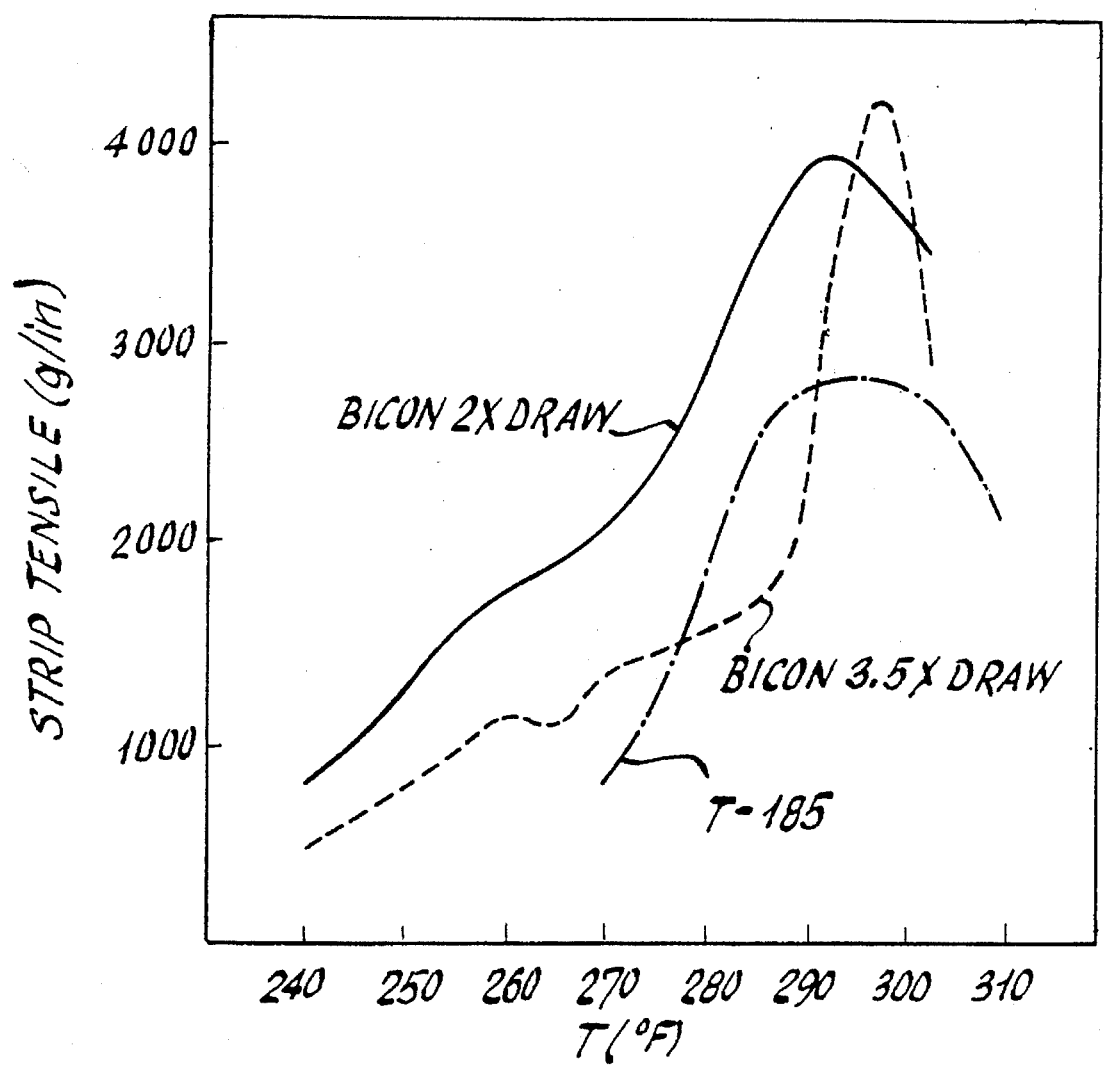
FIG. 2 is a graphic comparison of tensile strengths versus temperature for various fibers.

One gram samples of each fiber type were formed into a web using a lab-scale carding device. The carded webs were then bonded on a Beloit-Wheeler lab top calender using a 16%-diamond-bond pattern and a nip pressure of approximately 400 PLI. Strip tensile strengths were determined for samples bonded over a range of temperatures. Carded webs made from Hercules T-185 polypropylene fiber served as a control. The biconstituent-based fabrics demonstrate superior tensile properties over the polypropylene homofilament-based fabric (see Tables II, III, and IV, and FIG. 2).

EXAMPLE 2

Both polypropylene and PP/LLDPE dry blend samples were (separately) fed into a single-screw extrusion system equipped with a Barmag 3DD intensive mixer. Filaments were extruded and drawn to a final denier per filament of approximately 2.0. Line speeds and cold draw ratios were adjusted to produce filament samples having 2 X draw. Refer to Table I, samples 8319-IA and 8319-2, respectively.

Each fiber sample was separately carded and thermally bonded on a 36-inch-wide semicommercial line. Physical properties were then determined for the fabric samples. Data in Table V. The biconstituent fiber-based fabrics exhibited superior strip and grab tensiles, energies at yield (TEA), and tear values.

EXAMPLE 3

Staple biconstituent fiber containing 1% by weight of a substituted-sorbitol nucleating agent was prepared from dry blends of PP/LLDPE that was fed into a single-screw extrusion system equipped with a Barmag 3DD intensive mixer. Filaments were extruded and drawn to a final denier per filament of approximately 2.0. Line speeds and cold draw ratios were adjusted to produce filament samples having 3.5X draw. Refer to Table I, sample 8319-7.

The fiber was carded and thermally bonded on a 36-inch-wide semicommercial line. Data in Table VI. The strip and grab tensile, energies at yield, and tear values were superior to a similar fiber sample without nucleating agent.

EXAMPLE 4

Biconstituent fiber 8342 was prepared from a dry blend of 40% by weight of an ethylene/1-octene copolymer [LLDPE] having a melt index of 50 and a density of 0.925 g/cc with 60% by weight of controlled rheology polypropylene [PP] having a melt flow of 35. Multiconstituent fiber 8343 was prepared from a dry blend of 40% by weight LLDPE having a melt index of 50 and a density of 0.925 g/cc with 55% by weight of controlled rheology PP having a melt flow of 35 and with 5% by weight of ethylene/acrylic acid copolymer [EAA] composed of low density polyethylene having a melt index of 300 and an acrylic acid content of 20%. Melt blends were then separately prepared and extruded and pelletized using a single screw extrude equipped with a 6 row Rapra cavity-transfer mixer (CTM) and a strand die cutter. The polymer-blend pellets were then separately re-extruded into filaments and melt-drawn to a final denier per filament of 1.9 and 2.7, respectively.

One gram samples of each fiber type were formed into webs, bonded, and tested as described in Example 1. Filament and fabric tensile properties are indicated in Table VII.

End-Use Examples

EXAMPLE 5

8350-1A: PE film to PE/PP bicon fabric 8326-03 (1 osy)
8350-1B: PE film to PP fabric 8326-02 (1 osy)

To demonstrate the ability of multiconstituent fabric to form a fabric/film laminate, five-inch-wide fabric samples of a thermally bonded multiconstituent fiber-based nonwoven fabrics were "heat sealed" to polyethylene film. Laminate samples were prepared by heat-sealing a sandwich structure composed of carded fabric (8326-02 and 8326-03) (bottom)/polyethylene film (middle)/cover fabric (8326-02) (top). The cover fabric was used to insulate the low melting film from the sealing die. Fabric and film dimensions were 5"×12". Time, pressure, and die-temperature conditions were chosen that insured optimum adhesion of the fabric to the film while maintaining the film integrity. The heat sealer used was a Hut-Theller Precision Instruments West, Model ED (Petaluma, Calif.). Multiple heat-sealed samples were prepared by sealing across the width of the laminate sample. The die dimensions were flat, 3/8"×5", or 1.875 square inches Peel strengths were determined relative to a homofil fabric laminate control. Peel strengths are indicative of the level of adhesion between the fabric and film layers of the laminate. Peel strengths were determined using an Instron Model 4201 tensile tester. Strips 1-inch wide were cut from each sealed sample. The fabric was placed in the upper grip of the tensile tester and the film in the lower grip. A gauge length of 3-inches and a cross-head speed of 5-inches/minute were used. Peel strength properties are indicated in Table VIII. The level of adhesion was greater for the laminate which contained the multiconstituent fiber.

Examples 6 and 7 relate to breathable liquid barrier laminates with textile-like hand. Such laminates are suitable for use but not limited to use as medical and industrial garments, CSR wrap, surgical drape and housewrap. The laminates are prepared from a layer or layers of microfibrous (for example meltblown) polymer, such as polypropylene, sandwiched between two layers of nonwoven fabric containing multiconstituent fiber according to the present invention. The discontinuous polymer phase of the multiconstituent fiber occupies a portion of the surface of the fiber such that both polymers of the blend are available for thermal or sonic bonding and/or lamination. The fabric can be bonded prior to lamination or can be directly deposited on either side of the microfibrous layer just prior to lamination.

The microfibrous layer can be composed of meltblown fibers, wet laid pulps, or webs prepared by other known means. The microfibrous layer can be formed prior to the lamination or extruded or formed directly onto the multiconstituent nonwoven fabric prior to lamination. The microfibrous layer must be composed of a polymer which adheres to either the continuous or discontinuous polymer component of the multiconstituent fiber upon thermal or sonic lamination.

Thus, for instance, high melt flow isotactic polypropylene could be meltblown into a microfibrous web and then laminated to a fabric made from a polymer-blend fiber having polypropylene as one of the polymer constituents. Lamination can be with known calendering or sonic bonding technology. Bond pattern and processing conditions can be tailored to impart the desired combination of strength, barrier, drape, and textile aesthetics.

EXAMPLE 6

Samples of flat-calendered "sandwich-type" laminates were prepared from a polypropylene meltblown web weighing 20 grams per square meter and having a nominal filament diameter of 5 microns and two outer nonwoven layers composed of a multiconstituent fiber-based nonwoven fabric like that described in Example 1 and identified as Sample No. 8326-03 in Table V. The three webs were simultaneously unwound from a backstand and fed continuously into a heated calender nip. The lamination was effected using a 22" lab calender equipped with a heated smooth rubber roll and a heated smooth steel roll. The samples were prepared at varied calender roll surface temperatures, ranging from 318° F. to 306° F. for the steel roll and from 300° F. to 284° F., for the rubber roll. Nip pressure was held constant at 150 pounds per linear inch (pli), and line speed was held constant at 22 feet per minute.

Physical properties were determined for the resulting laminate samples and are identified as sample numbers 8331-1A through 8331-1F in Table IX. It is apparent from these data (8331-1A through 8331-1F) that a breathable liquid-barrier laminate can be obtained with excellent fabric tenacity.

EXAMPLE 7

A helically-bonded "sandwich-type" laminate was prepared by a procedure similar to that described in Example 6, but wherein the smooth rolls were replaced with steel rolls engraved with a diagonal line pattern such that the angle between the crisscross bond lines of the diagonal bonds opening in the machine direction (MD) measures 120 degrees, each line measuring 60 degrees off the MD axis and such that the raised bonding surfaces of each roll are flat and approximately 1 mm wide, separated by a recessed area measuring approximately 1.5 mm wide. A laminate fabric was produced at 22 fpm, 150 pli, at a calender roll surface temperature of 290° F. to 294° F.

Physical properties were determined for the fabric which is identified as sample number 8331-04 in Table IX. It is apparent from a comparison of the thickness, tensile, and barrier properties of this fabric with those in the same Table which have been flat-calendered that significantly different properties can be obtained for laminates composed of identical starting materials. Thickness is greatly increased over the flat-calendered samples. The loft of a fibrous web contributes to its ability to filter airborne or liquidborne particles efficiently. Air permeability is equivalent to breathability, a property associated with comfort in disposable garments. Air permeability combined with liquid barrier properties defines a fabric which can be used as a protective garment in a medical or industrial end use. In addition, the range of properties exhibited by these laminates demonstrate the flexibility of multiconstituent fabrics in laminate applications.

EXAMPLE 8

By use of the isotactic polypropylene/linear low density polyethylene polymer blend fiber-based fabric described in Table V (Sample No. 8326-04C), laminates were prepared that demonstrate the flexible bonding character of these novel substrates. Film and meltblown fabric were acquired whose polymer compositions matched either that of the continuous phase or that of the noncontinuous phase of the polymer-blend fiber. The grades of each polymer were selected that suited the respective substrate manufacturing processes, and are therefore not the identical polymers used in the manufacture of the multiconstituent fiber. "Sandwich-type" laminates were prepared using the procedure described in Example 7.

Physical property data appears in Table X. It is apparent from examination of this data that laminates exhibiting excellent tensile and barrier properties can be prepared by bonding the multiconstituent fiber-based fabric to substrates composed of a polymer selected from the same polymer groups represented in the multiconstituent fiber.

From the above description and specific Examples of the invention, many variation in the webs, composites, useful products, and processes of this invention will be apparent to those skilled in the relevant arts. Such variations are within the scope of the present invention as measure by the appended claims.

TABLE 1

| | BICONSTITUENT FILAMENT PROPERTIES | | | | |
| --- | --- | --- | --- | --- | --- |
| DB # | Polyblend Fiber Description | Cold Draw Ratio | Denier Per Filament | Filament Tenacity (g/den) | Elongation at Break (%) |
| 8319-1A | HIMONT Z30S PP | 2.2 | 2.10 (.10) | 3.12 (.12) | 51 (9.4) |
| 8319-1B | HIMONT Z30S PP | 3.5 | 1.95 (.10) | 4.72 (.39) | 27 (3.7) |
| 8319-2 | 40/60 PE(a)/PP | 2 | 1.96 (.11) | 2.04 (0.9) | 95 (40) |
| 8319-3 | 40/60 PE(a)/PP | 3.5 | 1.98 (.11) | 3.29 (.39) | 33 (7) |
| 8319-4 | 40/60 PE(b)/PP | 2 | 2.00 (.10) | 2.39 (.11) | 128 (32) |
| 8319-5 | 40/60 PE(b)/PP | 3.5 | 1.99 (.12) | 3.98 (.20) | 39 (4.8) |
| 8319-6 | PE(a)/PP + .5% NA | 2 | 1.96 (.12) | 1.85 (0.8) | 59 (18.6) |
| 8319-7 | PE(a)/PP + .5% NA | 3.5 | 1.94 (.10) | 3.75 (.17) | 35 (5.3) |

(#) - Denotes standard deviation, where n = 10.
PE(a) - DOW ASPUN (R) 6811, octene-1/ethylene copolymer, MI = 26
PE(b) - DOW ASPUN (R) 6815, octene-1/ethylene copolymer, MI = 12
PP - HIMONT Z30S Controlled Rheology Grade Polypropylenes, MF = 26
NA - MILAD 5L71-10 Nucleating Agent. 10% conc. in LLPDE.

TABLE II

LAB TOP FABRIC PROPERTIES OF BICONSTITUENT BASED THERMAL BOND FABRICS
(Fiber: 40/60 PE/PP, 8319-2, 2X DRAW, TABLE I)

| DATA BOOK # | CALENDER SURFACE TEMPERATURE | | STRIP TENSILE | | | TEA |
| --- | --- | --- | --- | --- | --- | --- |
| | EMB. F | SM. F | (g/in) | SD | % E | (in/g/in2) |
| 8324-1 | 240 | 244 | 819 | 87 | 11 | 116 |
| 2 | 250 | 254 | 1263 | 55 | 17 | 224 |
| 3 | 255 | 259 | 1811 | 86 | 15 | 317 |
| 4 | 260 | 264 | 1594 | 48 | 19 | 302 |
| 5 | 265 | 269 | 1817 | 185 | 20 | 347 |
| 6 | 270 | 274 | 2058 | 184 | 22 | 451 |
| 7 | 275 | 279 | 2292 | 100 | 23 | 484 |
| 8 | 280 | 284 | 2829 | 141 | 21 | 554 |
| 9 | 289 | 285 | 3571 | 177 | 28 | 821 |
| 10 | 294 | 290 | 3938 | 215 | 27 | 804 |
| 11 | 299 | 295 | 3747 | 355 | 32 | 930 |
| 12 | 305 | 300 | 3360 | 272 | 27 | 686 |

TABLE III (FIBER: 40/60 PE/PP, 8319-3, 3.5X DRAW, TABLE I)

| | | | | | | |
|---|---|---|---|---|---|---|
| 8324-13 | 240 | 245 | 469 | 53 | 6 | 49 |
| 14 | 245 | 249 | 625 | 42 | 9 | 78 |
| 15 | 250 | 254 | 765 | 52 | 9 | 100 |
| 16 | 255 | 259 | 977 | 58 | 9 | 123 |
| 17 | 260 | 264 | 1115 | 216 | 10 | 153 |
| 18 | 265 | 269 | 1067 | 185 | 7 | 128 |
| 19 | 270 | 274 | 1351 | 186 | 9 | 164 |
| 20 | 275 | 279 | 1368 | 93 | 8 | 158 |
| 21 | 280 | 284 | 1568 | 147 | 7 | 182 |
| 22 | 289 | 285 | 1868 | 121 | 12 | 247 |
| 23 | 294 | 290 | 3230 | 173 | 11 | 381 |
| 24 | 299 | 295 | 4228 | 181 | 14 | 559 |
| 25 | 305 | 300 | 2704 | 211 | 26 | 644 |

TABLE IV (FIBER: HERCULES T-185)

| | | | | | | |
|---|---|---|---|---|---|---|
| 8324-26 | 270 | 265 | 834 | 29 | 20 | 196 |
| 27 | 280 | 275 | 1611 | 103 | 33 | 573 |
| 28 | 290 | 285 | 2705 | 51 | 73 | 1757 |
| 29 | 300 | 295 | 2809 | 361 | 54 | 1289 |
| 30 | 310 | 305 | 2136 | 95 | 14 | 232 |

NOTES: All samples produced at 500 PLI, 22 FPM, 18% bond area.

TABLE V

PHYSICAL PROPERTIES OF SELECTED STAPLE BICONSTITUENTS

| DATABOOK # | FIBER SAMPLE ID. (TABLE I) | FIBER DENIER (dpf) | CALENDER SURFACE °F. E/S | B.W. (gsy) | LOFT (mils) |
|---|---|---|---|---|---|
| 8326-02 | PP FIBER 8319-1 | 2 | 270/300 | 28.8 | 15.9 |
| 8326-03 | FIBER 8319-2. 2X | 1.95 | 270/295 | 32.6 | 13.4 |
| 8326-04 | SAME AS ABOVE | 1.95 | 300/300 | 31.6 | 13.3 |

| | STRIP TENSILES | | | | | | GRAB TENSILES | | | | ELMENDORF TEAR | | |
|---|---|---|---|---|---|---|---|---|---|---|---|---|---|
| | MD # | | | CD # | | | | | | | | | |
| DATABOOK # | (losy) (g/in) | % E | TEA | (losy) (g/in) | % E | TEA | MD (lbs) | % E | CD (lbs) | % E | MD (g) | CD (g) | SOFT (psu) |
| 8326-02 | 1124 | 35 | 164 | 288 | 39 | 78 | 4.8 | 16 | 2.1 | 33 | 109 | 144 | 1.7 |
| 8326-03 | 2098 | 24 | 415 | 501 | 59 | 256 | 10.5 | 24 | 4.6 | 58 | 138 | 200 | 0.9 |
| 8326-04 | 1972 | 14 | 207 | 704 | 40 | 255 | 9.2 | 15 | 6.1 | 46 | 72 | 149 | −0.8 |

TABLE VI

PHYSICAL PROPERTIES OF SELECTED STAPLE BICONSTITUENTS

| DATABOOK # | FIBER SAMPLE ID. (TABLE I) | FIBER DENIER (dpf) | CALENDER SURFACE °F. E/S | B.W. (gsy) | LOFT (mils) |
|---|---|---|---|---|---|
| 8326-05 | FIBER 8319-3 | 1.98 | 270/290 | 30.5 | 12.9 |
| 8326-07 | FIBER 8319-6 | 1.93 | 270/290 | 31 | 14.1 |

| | STRIP TENSILES | | | | | | GRAB TENSILES | | | | ELMENDORF TEAR | | |
|---|---|---|---|---|---|---|---|---|---|---|---|---|---|
| | MD # | | | CD # | | | | | | | | | |
| DATABOOK # | (losy) (g/in) | % E | TEA | (losy) (g/in) | % E | TEA | MD (lbs) | % E | CD (lbs) | % E | MD (g) | CD (g) | SOFT (psu) |
| 8326-05 | 1293 | 29 | 173 | 343 | 43 | 93 | 6.1 | 15 | 2.7 | 32 | 122 | 178 | 0.4 |
| 8326-07 | 1728 | 27 | 262 | 464 | 36 | 31 | 8.2 | 18 | 4 | 40 | 178 | 229 | 0.7 |

TABLE VII

FILAMENT AND FABRIC PROPERTIES OF SELECTED MULTICONSTITUENT FIBERS

| FABRIC SAMPLE No. 1 | FILAMENT-PROPERTIES (1) | | | | FABRIC PROPERTIES (2) | | |
|---|---|---|---|---|---|---|---|
| | (dpf) | TENACITY (gpd) | ELONG. (%) | TOUGHNESS (gpd) | TENSILE (g/in) | ELONG. (%) | TEA (in/g/in2) |
| 8342-1 | 1.9 | 1.52 | 420 | 4.5 | 2808 | 74 | 993 |
| STD. DEV. | | (0.16) | (61) | (1.0) | (251) | (17) | |
| 8343-1 | 2.7 | 1.0 | 405 | 2.7 | 3276) | 30 | 727 |
| STD. DEV | | (0.21) | (124) | (0.8) | (377) | (6) | |

STD DEV: N = 10
(1) 8342-1 Fabric: melt blend fiber composed of 40:60 wt % PE:PP
8343-1 Fabric: melt blend fiber composed of 40:55:5 wt. % PE:PP:EAA
(2) Fabric properties normalized to 1.0 ounce yd2 basis weight

TABLE VIII

HEAT SEAL PEEL STRENGTH FOR BICONSTITUENT-FILM LAMINATE

| SAMPLE NO. | PEEL STRENGTH pk load (g/in) | ELONGATION at pk (%) | PEEL STRENGTH TEA (in/g/in2) |
|---|---|---|---|
| 8350-1A | 559 | 24 | 175 |
| 3850-1B | 443 | 27 | 86 |

Die Geometry: ⅜" × 5", flat
Time: 500 msec
Temp: top - 245 F.; lower - 245 F.
Pressure: 550 psi

TABLE IX

PE/PP BICONSTITUENT LAMINATES
PHYSICAL PROPERTIES

| DATABOOK # | SAMPLE DESCRIPTION (1) | B.W. (gsy) | MODEL 549 THICK. (mils) | LAMINATION TEMP. (F.) | STRIP TENSILES (2) MD (g/in) | % E | TEA | CD (g/in) | % E | TEA | ELMENDORF TEAR MD (g/in) | CD (g/in) | GURLEY POROSITY (sec) (20 oz) | (5 oz) | HYDROSTATIC HEAD (cm) | MASON JAR (sec) |
|---|---|---|---|---|---|---|---|---|---|---|---|---|---|---|---|---|
| 8331-1A | FC BICON./PPMB/BICON | 106 | 11.7 | 318/300 | 9078 | 15 | 1306 | 3940 | 6 | 250 | 360 | 770 | 56 | 275 | 24.1 | 10 |
| 8331-1B | FC BICON./PPMB/BICON | 102 | 9.2 | 316/297 | 9340 | 15 | 1078 | 4286 | 8 | 266 | 325 | 575 | 93 | >5 min. | 25.6 | 70 |
| 8331-1C | FC BICON./PPMB/BICON | 90 | 8.5 | 313/294 | 9508 | 16 | 984 | 3871 | 8 | 211 | 290 | 490 | 120 | >5 min. | 22.5 | 39 |
| 8331-1D | FC BICON./PPMB/BICON | 93 | 8.6 | 310/290 | 7963 | 11 | 674 | 4002 | 6 | 194 | 260 | 580 | 66 | >5 min. | 22 | 26 |
| 8331-1E | FC BICON./PPMB/BICON | 89 | 8.3 | 308/287 | 9189 | 14 | 855 | 4320 | 8 | 224 | 310 | 520 | 65 | >5 min. | 19.6 | 33 |
| 8331-1F | FC BICON./PPMB/BICON | 96 | 9.2 | 306/284 | 8440 | 14 | 1016 | 3796 | 18 | 306 | 320 | 600 | 29 | >5 min. | 18.9 | 28 |
| 8331-04 | HELIC. BIC./PPMB/BIC | 86 | 23.6 | 290/294 | 5863 | 15 | 625 | 3211 | 17 | 353 | 330 | 460 | inst. | 7 | 13.2 | 3 |

NOTES:
(1) FC - Flat Calendered
Helic. - Crisscross bond pattern from helical rolls
PPMB - Polypropylenes melt blown (20 gse)
Bicon. - Polyethylene/polypropylene biconstituent fiber based fabric - 8326-03
(2) Tensiles corrected to 3 osy unit weight

TABLE X

PHYSICAL PROPERTIES OF POLYETHYLENE/POLYPROPYLENE
BICONSTITUENT FABRIC LAMINATES

| SAMPLE # | DESCRIPTION (1) | CALENDER TEMP. (2) (F.) | UNIT WT. (gsy) | CALIPER (3) (mils) | ** GRAB TENSILES ** MD (lbs) | El. (%) | CD (lbs) | El. (%) | ELM. TEAR MD (g) | CD (g) | MULLEN BURST (psi) | (4) POROSITY (5 oz) (sec) | (20 oz) (sec) | (5) MASON JAR (sec) | HYDRO-STATIC HEAD (cm) |
|---|---|---|---|---|---|---|---|---|---|---|---|---|---|---|---|
| 8333-05 | BICON/PE FILM/BICON | 252/263 | 76.6 | 28.1 | 22 | 27 | 11.7 | 38 | 400 | 540 | 21 | NR | 53.3 | 3.16 | 18.4 |
| 8333-06 | BICON/PP FILM/BICON | 287/288 | 70.9 | 26.4 | 22.7 | 30 | 11.1 | 42 | 330 | 430 | 19 | NR | 98 | 163 | 23.7 |
| 8333-04 | BICON/PE-MB/BICON | 268/260 | 93.6 | 26.8 | 23.1 | 24 | 10.2 | 34 | 350 | 400 | 20 | 1.57 | NR | inst. | 16.1 |
| 8331-04 | BICON/PP-MB/BICON | 290/294 | 86.3 | 27.2 | 25.3 | 25 | 10.8 | 36 | 320 | 380 | 19 | 7.1 | NR | 3 | 13.2 |

NOTES:
All PE is 1-octene, linear low density polyethylene, unless otherwise stated.
(1) Bicon - Bicostituent fiber-based fabric (8326-04 carded thermalbond, 40:60, PE:PP), 1 OSY
PE Film - Low density polyethylene film obtained from Edison Plastic, 1 Mil.
PP Film - Polyethylene film obtained from Edison Plastic, 1 Mil.
PE-MB - Polyethylene meltblown fabric, 20 gsm
(2) Calendar - helical steel/helical steel, NIP pressure 350 PLI, line speed = 12.5 FPM
(3) Fabric caliper measured using a 551-M caliper tester
(4) NR - No reading, process either too fast or too slow for accurate measurement
(5) Inst - Instantaneous

EXAMPLE 9

Isotactic polypropylene of a melt flow rate of 25 was dry blended with an ethylene/1-octene linear low density polyethylene [LLDPE] having a melt index of 26 and a density of 0.940 grams/cc at polyethylene levels of 2.5 weight percent, 8 percent, 15 percent and 25 percent by a procedure similar to that described in Example 1, and the polymer blends were melt-spun from a commercial S-Tex spinbonding apparatus (S-Tex is a trademark of Sodoca S.à.r.l. of Biesheim France, a member of The Fiberweb Group) to form a spunbonded web for each polymer blend. For each different polyethylene content, an SMS (spunbond/meltblown/spunbond) nonwoven fabric laminate was formed by sandwiching a microfibrous meltblown polypropylene web similar to that of Example 6 between two similar spunbonded webs. The three nonwoven webs were laminated by passing through a heated calender having a 14% diagonal diamond embossed pattern to form a spunbond/meltblown/spunbond (SMS) nonwoven fabric laminate. An SMS nonwoven fabric laminate control was prepared in a similar manner using the same meltblown layer and using 100% polypropylene homofilaments in the spunbonded layers instead of the multiconstituent filaments.

A scanning electron microscope (SEM) was used to examine the bond areas of the resulting spunbond/meltblown/spunbond (SMS) laminates. The SEM photomicrographs revealed that presence of the polyethylene component in the multiconstituent spunbonded filaments has the effect of reducing stress fracture in the spunbonded fibers as they enter the bond point. These fibers appear to deform smoothly as they approach and enter the bond site, exhibiting polymer flow behavior rather than the fracturing and surface fissure development that is evident in the 100% polypropylene control.

Figure 3:
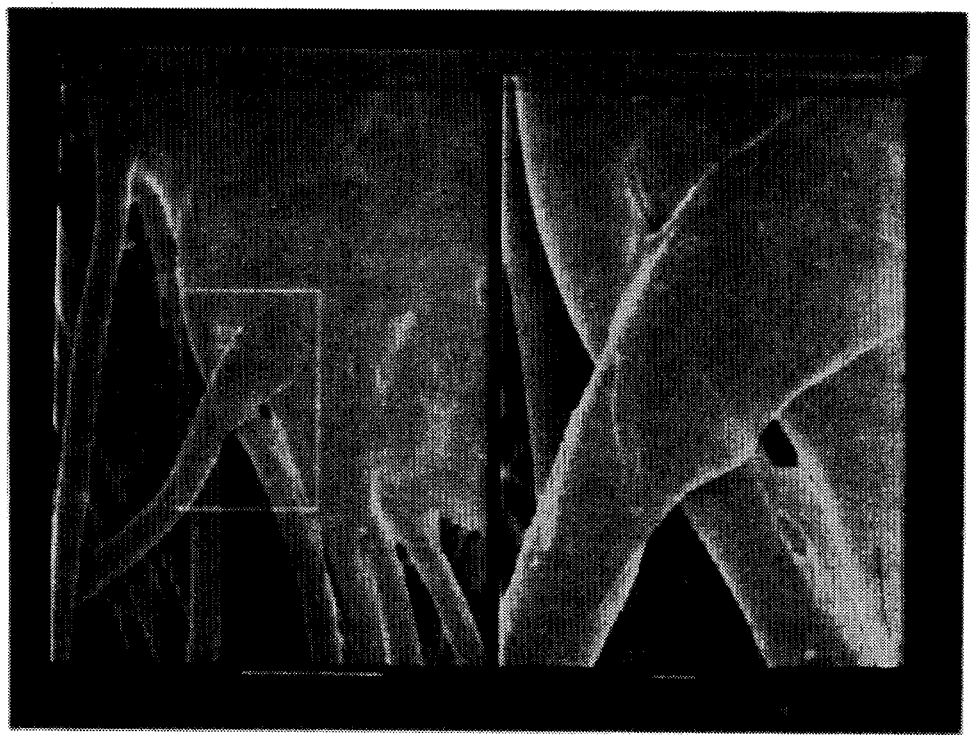
FIG. 3 is a scanning electron photomicrograph showing a thermally bonded nonwoven fabric in accordance with the prior art.

FIG. 3 is a top view of a bond point of the 100% polypropylene control fabric, at 204× and 644× magnification. The large, relatively smooth area is the bond site, and the strandlike elements are the polypropylene spunbond fibers. The sample shows considerable stress fracture and surface fissure development of the spunbond fiber surface at the approach to and entry into the bond site. This phenomenon and its effect on fabric strength in thermal bonded polypropylene fabrics of this type has been previously reported by S. B. Warner, "Thermal Bonding of Polypropylene Fibers", *Textile Research Journal*, March 1989 pp. 151–159.

Figure 4:
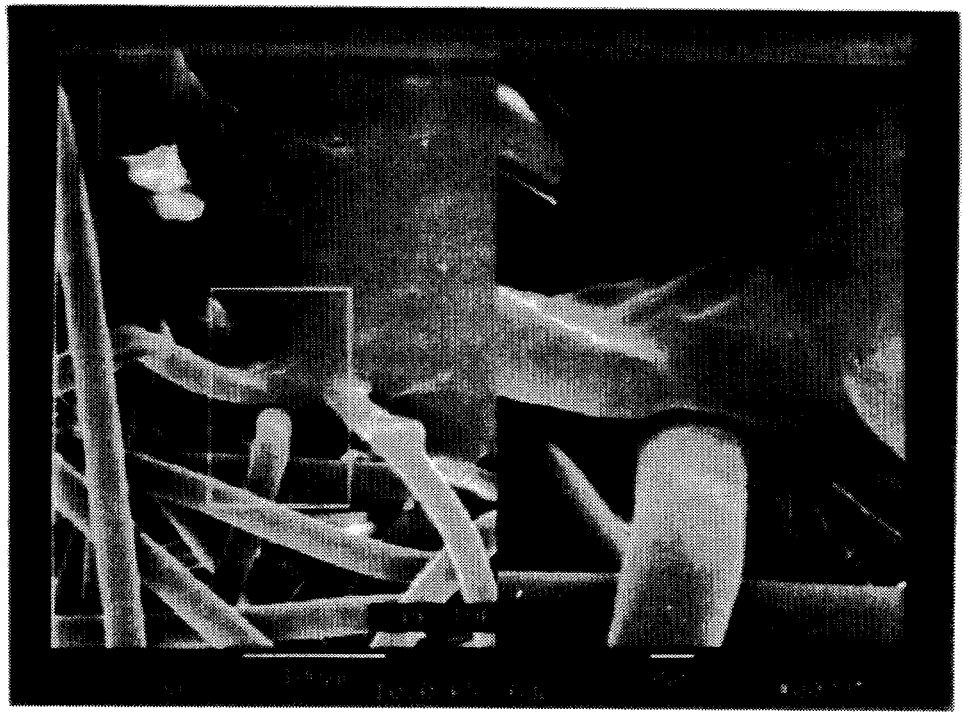
FIGS. 4 and 5 are scanning electron photomicrographs showing thermally bonded nonwoven fabrics in accordance with the present invention.
Figure 5:
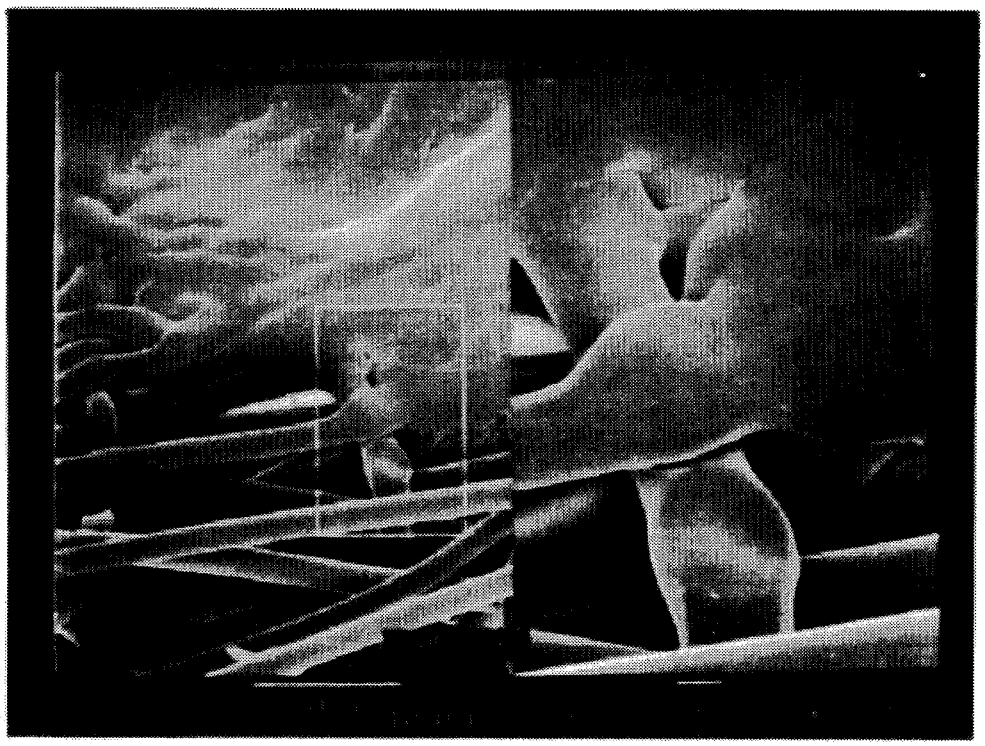

FIG. 4 is a top view of an SMS nonwoven fabric laminate in accordance with the present invention, in which the spunbonded fibers are multiconstituent fibers containing 8% by weight polyethylene dispersed in an isotactic polypropylene matrix. In contrast to FIG. 3, in this specimen one can observe deformation of the spunbond fibers near their juncture with the bond site. FIG. 5 is a view similar to FIG. 4, but wherein the multiconstituent fibers contain 25% by weight polyethylene dispersed in an isotactic polypropylene matrix. In this specimen, the deformation and flow of the fibers in the vicinity of the bond site are quite evident. In the enlarged view, it will be seen that the fibers have actually become flattened at their crossover junctions near the bond site. This flow behavior is a result of the presence of the lower melting polyethylene component, and contributes to development of good bond strength through a bond that is both adhesive as well as cohesive, as opposed to a principally cohesive bond.

The mechanical effects of the presence of the polyethylene in the spunbond fibers on the SMS bond and bonding efficiency were examined in two ways. A Theller Heat Sealer was used in a laboratory setting to determine the optimum temperature setting for sample preparation. Hand samples were also prepared using a commercial calender for bonding. In both cases, an Instron Peel Strength test was used to evaluate the samples. Total Energy Absorbed (TEA) was the value used to determine the difference among the materials. This value includes both tensile strength and elongation, thereby eliminating the potential to claim added strength on a material that is actually brittle. Under these conditions, it was determined that the added polyethylene content does give a thermal bond that is stronger than the 100% polypropylene control. However, a reduction in peel strength was observed in the samples prepared with a commercial calender at polyethylene contents of 15 and 25 percent.

EXAMPLE 10

Samples of a spunbonded nonwoven fabric were prepared by a procedure similar to that described in Example 9, with the polyethylene content of the multiconstituent fibers at levels of 0, 8, 15 and 25 percent. The strength values of the fabric samples were measured both in the initial state and after being subjected to a steam autoclave at a temperature of 275° F. (135° C.) for six minutes. The results are set forth in Tables XI and XII. These tests show that for fabrics intended for CSR wrap end use, the polyethylene content of the multiconstituent fiber must be kept below 25 weight percent. For the rest of the data, all samples show a decline in strength after autoclaving, as does the 100 percent polypropylene homofilament control.

TABLE XI

| | | EFFECT OF AUTOCLAVING ON STRENGTH | | | | | | |
|---|---|---|---|---|---|---|---|---|
| | | STRENGTH VALUES | | | | | | |
| | | GRAB TENSILE | | GRAB ELONG, % | | TRAP TEAR* | | HAND |
| SAMPLE # | % PE | BEFORE | AFTER | BEFORE | AFTER | BEFORE | AFTER | AFTER |
| 1339-01 | 0 MD | 18.9 | 18.5 | 79 | 52 | 8.0 | 6.6 | NC |
| | CD | 11.4 | 9.0 | 106 | 59 | 4.7 | 2.3 | |
| 1339-02 | 8 MD | 10.9 | 9.3 | 66 | 28 | 6.6 | 4.4 | NC |
| | CD | 6 | 3.9 | 71 | 45 | 2.9 | 2.2 | |
| 1339-03 | 15 MD | 17.2 | 14.2 | 56 | 35 | 9.7 | 4.0 | NC |
| | CD | 10.1 | 5.0 | 96 | 48 | 3.5 | 1.9 | |
| 1339-04 | 25 | X | X | X | X | X | X | MELTED |

*= lb.
X = sample did not survive autoclave.

TABLE XII

PERCENTAGE OF STRENGTH LOSS AFTER AUTOCLAVING

| | | PERCENT LOSS | | | | | |
|---|---|---|---|---|---|---|---|
| SAMPLE # | % PE | GRAB MD | TENSILE CD | GRAB MD | ELONG CD | TRAP MD | TEAR CD |
| 1339-01 | 0 | 2 | 21 | 34 | 44 | 18 | 51 |
| 1339-01 | 8 | 15 | 35 | 58 | 36 | 33 | 25 |
| 1339-03 | 15 | 18 | 50 | 38 | 50 | 59 | 46 |
| 1339-04 | 25 | X | X | X | X | X | X |

X = sample did not survive autoclave

EXAMPLE 11

The flexural rigidity of the 8% PE SMS fabric of Example 9 was measured using ASTM Standard Test Method D 1388 (Option A—Cantilever Test) and compared to a commercially available SMS fabric in which the spunbonded component is formed from polypropylene homofilaments (Kimgard H. D. from Kimberly-Clark Corporation). As shown in Table XIII below, the fabric formed from the polyethylene/ polypropylene multiconstituent filaments had flexural rigidity values which were approximately half that of the fabric formed from the polypropylene homofilaments, both in the machine and cross machine directions.

TABLE XIII

| FLEXURAL RIGIDITY OF SMS FABRICS | | |
|---|---|---|
| Sample | MD | CD |
| 8% PE/PP | 612 | 232 |
| 100% PP (Kimgard HD) | 1220 | 492 |

EXAMPLE 12

A spunbonded nonwoven fabric was produced by melt spinning a 90/10 blend (by weight) of nylon 6 and linear low density polyethylene. The fiber size produced ranged from about 2 to 6 denier. An SMS nonwoven fabric laminate was formed by sandwiching a microfibrous meltblown polyethylene web similar to that of Example 6 between two of the nylon/PE spunbonded webs and thermally bonding through a heated calender as in Example 9. For comparison, a control SMS fabric was formed in a similar manner, but with the spunbond component being formed from 100% nylon 6. An improvement in softness (hand) was noted in the blend fabric as compared to the control. Hand samples of the blend SMS fabric showed a 25% increase in repellency, as measured by hydrohead, versus the 100% nylon SMS control. Bonding of the three layers is achieved at a lower temperature in the blend SMS as compared to the control. In laboratory tests, bonding was initiated at 20° F. lower temperature for the blend vs. the control, at constant pressure.

That which is claimed is:

1. A nonwoven fabric laminate comprising:

a thermally bonded nonwoven web comprising multiconstituent fibers formed of a highly dispersed blend of at least two different thermoplastic polymers which are present as a dominant continuous phase and at least one noncontinuous phase dispersed therein, the polymer of said at least one noncontinuous phase having a melting temperature below that of said continuous phase, and said lower melting noncontinuous phase comprising from about 2.5 to 20 percent by weight of the fiber, wherein said multiconstituent fibers are configured such that said at least one noncontinuous phase occupies a substantial portion of the fiber surfaces;

at least one other web bonded to said nonwoven web; and a multiplicity of thermal bonds formed from the polymer of said multiconstituent fibers and bonding the multiconstituent fibers of said thermally bonded web to one another and to said at least one other web, said multiconstituent fibers exhibiting deformation and polymer flow in the vicinity of their juncture with said thermal bonds.

2. A nonwoven fabric laminate according to claim 1, wherein the multiconstituent fibers of said thermally bonded web comprise from 5 to 15 percent by weight of said lower melting polymer phase.

3. A nonwoven fabric laminate according to claim 1, wherein the multiconstituent fibers of said thermally bonded web are in the form of discrete staple fibers.

4. A nonwoven fabric laminate according to claim 1, wherein the multiconstituent fibers of said thermally bonded web are in the form of continuous filaments.

5. A nonwoven fabric laminate according to claim 1, wherein said at least one other web comprises at least one polyolefin film.

6. A nonwoven fabric laminate according to claim 1, wherein said at least one other web comprises at least one microfibrous layer.

7. A nonwoven fabric laminate according to claim 1, wherein said multiconstituent fibers include a continuous phase of a polymer selected from the group consisting of polyolefins, polyamides, and polyesters.

8. A nonwoven fabric laminate according to claim 7, wherein the polymer of said dominant continuous phase is a polyolefin selected from the group consisting of isotactic polypropylene, propylene-ethylene random copolymer, propylene-ethylene block copolymer, poly (4-methyl-1-pentene), polystyrene, or linear low density polyethylene.

9. A nonwoven fabric laminate according to claim 8, wherein the polymer of said dominant continuous phase is polypropylene and the polymer of said at least one noncontinuous phase is polyethylene.

10. A nonwoven fabric laminate according to claim 9, wherein the multiconstituent fiber comprises from about 5 to 15 percent by weight polyethylene and the balance isotactic polypropylene.

11. A nonwoven fabric laminate according to claim 7, wherein the polymer of said dominant continuous phase is a polyamide and the polymer of said at least one noncontinuous phase is polyethylene.

12. A nonwoven fabric laminate according to claim 7, wherein the polymer of said dominant continuous phase is a polyester and the polymer of said at least one noncontinuous phase is polyethylene.

13. A nonwoven fabric laminate according to claim 1, wherein said thermally bonded nonwoven web comprises a spunbonded web of said multiconstituent fibers, and at least one other web comprises at least one microfibrous layer.

14. A nonwoven fabric laminate according to claim 13, wherein the polymer of said dominant continuous phase comprises polypropylene and the polymer of said at least one noncontinuous phase comprises polyethylene.

15. A nonwoven fabric laminate comprising:

first and second thermally bonded spunbonded webs of multiconstituent fiber, and at least one microfibrous web disposed between said first and second spunbonded webs, the multiconstituent fiber of said first and second spunbonded webs comprising continuous filaments formed of a highly dispersed blend of at least two different thermoplastic polymers which are present as a dominant continuous phase and at least one noncontinuous phase dispersed therein, the polymer of said at least one noncontinuous phase having a melting temperature below that of said continuous phase, wherein said multiconstituent fibers are configured such that said at least one noncontinuous phase occupies a substantial portion of the fiber surfaces; and a multiplicity of thermal bonds formed in said spunbonded webs from the polymer of said multiconstituent fiber thereof, said thermal bonds bonding the continuous filaments of the spunbonded webs to one another and also bonding the spunbonded webs to said at least one microfibrous web, said multiconstituent fiber exhibiting deformation and polymer flow in the vicinity of its juncture with said thermal bonds.

16. A nonwoven fabric laminate according to claim 15, wherein said lower melting noncontinuous phase comprises from about 2.5 to about 20 percent by weight of the multiconstituent fiber.

17. A nonwoven fabric laminate according to claim 15, wherein the polymer of said dominant continuous phase comprises polypropylene and the polymer of said at least one noncontinuous phase comprises polyethylene.

18. A nonwoven fabric laminate according to claim 15, wherein the polymer of said dominant continuous phase comprises polyamide and the polymer of said at least one noncontinuous phase comprises a polyolefin.

19. A nonwoven fabric laminate according to claim 15, wherein said multiconstituent filaments of said spunbonded webs exhibit deformation and polymer flow in the vicinity of the juncture with said thermal bonds.

20. A nonwoven fabric laminate comprising:

first and second thermally bonded spunbonded webs of multiconstituent fiber, and at least one meltblown microfibrous polypropylene web disposed between said first and second spunbonded webs, the multiconstituent fiber of said first and second thermally bonded spunbonded webs comprising continuous filaments formed of a highly dispersed blend of thermoplastic olefin polymers, including isotactic polypropylene present as a dominant continuous phase and from about 2.5 to 20 percent by weight of a lower melting polyethylene polymer forming a noncontinuous phase dispersed in said continuous polypropylene phase, wherein said multiconstituent fibers are configured such that said noncontinuous polyethylene phase occupies a substantial portion of the fiber surfaces; and a multiplicity of discrete thermal bonds formed in said spunbonded webs from the polymer of said multiconstituent fiber thereof, said thermal bonds bonding the continuous filaments of the spunbonded webs to one another and also bonding the spunbonded webs to said at least one meltblown microfibrous polypropylene web, said multiconstituent fiber exhibiting deformation and polymer flow in the vicinity of its juncture with said thermal bonds.

21. A nonwoven fabric laminate comprising:

first and second spunbonded webs of multiconstituent fiber, and at least one meltblown microfibrous polypropylene web disposed between said first and second spunbonded webs, the multiconstituent fiber of said first and second thermally bonded spunbonded webs comprising continuous filaments formed of a highly dispersed blend of a polyamide polymer present as a dominant continuous phase and from about 2.5 to 20 percent by weight of a lower melting polyethylene polymer forming a noncontinuous phase dispersed in said continuous polyamide phase; and a multiplicity of discrete thermal bonds formed in said spunbonded webs from the polymer of said multiconstituent fiber thereof, said thermal bonds bonding the continuous filaments of the spunbonded webs to one another and also bonding the spunbonded webs to said at least one meltblown microfibrous polypropylene web.

22. A nonwoven fabric laminate comprising:

first and second spunbonded webs of multiconstituent fiber, and at least one meltblown microfibrous polypropylene web disposed between said first and second spunbonded webs, the multiconstituent fiber of said first and second thermally bonded spunbonded webs comprising continuous filaments formed of a highly dispersed blend of a polyester polymer present as a dominant continuous phase and from about 2.5 to 20 percent by weight of a lower melting polyethylene polymer forming a noncontinuous phase dispersed in said continuous polyester phase; and a multiplicity of discrete thermal bonds formed in said spunbonded webs from the polymer of said multiconstituent fiber thereof, said thermal bonds bonding the continuous filaments of the spunbonded webs to one another and also bonding the spunbonded webs to said at least one meltblown microfibrous polypropylene web.

23. A thermally bonded nonwoven fabric comprising multiconstituent fibers formed of a highly dispersed blend of at least two different thermoplastic polymers which are present as a dominant continuous phase and at least one noncontinuous phase dispersed therein, the polymer of said at least one noncontinuous phase having a melting temperature below that of said continuous phase, and said lower melting noncontinuous phase comprising from about 2.5 to about 20 percent by weight of the fiber, wherein said multiconstituent fibers are configured such that said at least one noncontinuous phase occupies a substantial portion of the fiber surfaces; and a multiplicity of thermal bonds formed from the polymer of said multiconstituent fibers and bonding the multiconstituent fibers to one another, said multiconstituent fiber exhibiting deformation and polymer flow in the vicinity of its juncture with said thermal bonds.

24. A nonwoven fabric according to claim 23, wherein said multiconstituent fibers exhibit deformation and polymer flow in the vicinity of the their juncture with said thermal bonds.

25. A nonwoven fabric according to claim 23, wherein the multiconstituent fibers comprise from 5 to 15 percent by weight of said lower melting polymer phase.

26. A nonwoven fabric according to claim 23 wherein the polymer of said dominant continuous phase is polypropylene and the polymer of said at least one noncontinuous phase is polyethylene.

27. A thermally bonded nonwoven fabric comprising a spunbonded web of multiconstituent continuous filaments formed of a highly dispersed blend of thermoplastic olefin polymers, including isotactic polypropylene present as a dominant continuous phase and from about 2.5 to 20 percent by weight of a lower melting polyethylene polymer forming a noncontinuous phase dispersed in said continuous polypropylene phase, wherein said multiconstituent fibers are configured such that said noncontinuous polyethylene phase occupies a substantial portion of the fiber surfaces; and a multiplicity of discrete thermal bonds formed in said spunbonded web from the polymer of said multiconstituent filaments thereof bonding the continuous filaments of the spunbonded webs to one another, said multiconstituent fiber exhibiting deformation and polymer flow in the vicinity of its juncture with said thermal bonds.

28. A nonwoven fabric comprising a spunbonded web of multiconstituent continuous filaments formed of a highly dispersed blend of a polyamide polymer present as a dominant continuous phase and from about 2.5 to 20 percent by weight of a lower melting polyolefin polymer forming a noncontinuous phase dispersed in said continuous polyamide phase; and a multiplicity of discrete thermal bonds formed in said spunbonded web from the polymer of said multiconstituent filaments thereof bonding the continuous filaments of the spunbonded webs to one another.

29. A nonwoven fabric comprising a spunbonded web of multiconstituent continuous filaments formed of a highly dispersed blend of a polyester polymer present as a dominant continuous phase and from about 2.5 to 20 percent by weight of a lower melting polyolefin polymer forming a noncontinuous phase dispersed in said continuous polyester phase; and a multiplicity of discrete thermal bonds formed in said spunbonded web from the polymer of said multiconstituent filaments thereof bonding the continuous filaments of the spunbonded webs to one another.

* * * * *

UNITED STATES PATENT AND TRADEMARK OFFICE
CERTIFICATE OF CORRECTION

PATENT NO. : 5,593,768

DATED : January 14, 1997

INVENTOR(S) : Gessner

It is certified that error appears in the above-identified patent and that said Letters Patent is hereby corrected as shown below:

Column 4, line 4, "1pentene" should be -- 1-pentene --.

Column 4, line 36, after "Chapter 16" insert -- . --.

Column 9, line 48, after "inches" insert -- . --.

Column 12, Table I, in line 4 of the notes, "Polypropylenes" should be -- Polypropylene --.

Column 14, last line of Table VI, column 7, "31" should be -- 131 --.

Columns 15-16, Table VII, column 1, "DEV" should be -- DEV. --.

Columns 15-16, Table VII, column 6, "3276)" should be -- 3276 --.

Columns 15-16, Table VIII, column 1, "3850-1B" should be -- 8350-1B --.

Columns 17-18, Table IX, in line 4 of the NOTES, "Polypropylenes" should be -- Polypropylene --.

UNITED STATES PATENT AND TRADEMARK OFFICE
CERTIFICATE OF CORRECTION

PATENT NO. : 5,593,768

DATED : January 14, 1997

INVENTOR(S) : Gessner

Page 2 of 3

It is certified that error appears in the above-indentified patent and that said Letters Patent is hereby corrected as shown below:

Columns 19-20, third from end sub-heading "POROSITY" should be -- GURLEY POROSITY --.

Columns 19-20, line 5 of NOTES, "PP Film-Polyethylene" should be -- PP Film-Polypropylene --.

Columns 19-20, line 7 of NOTES, "Calendar" should be -- Calender --.

Column 21, line 44, after "1989" insert -- , --.

UNITED STATES PATENT AND TRADEMARK OFFICE
CERTIFICATE OF CORRECTION

PATENT NO. : 5,593,768
DATED : January 14, 1997
INVENTOR(S) : Gessner

It is certified that error appears in the above-indentified patent and that said Letters Patent is hereby corrected as shown below:

Columns 21-22, Table XI, third column, line 4, "6" should be -- 6.0 --.

Column 26, line 59, "fiber" should be -- fibers --.

Column 26, line 60, "its" should be -- their --.

Colun 27, line 18, "fiber" should be -- fibers --.

Column 27, line 20, "its" should be -- their --.

Signed and Sealed this

Twenty-ninth Day of April, 1997

Attest:

BRUCE LEHMAN

Attesting Officer

Commissioner of Patents and Trademarks